(12) United States Patent
Weiss et al.

(10) Patent No.: US 10,444,183 B2
(45) Date of Patent: Oct. 15, 2019

(54) SENSOR ARRANGEMENT

(71) Applicant: Endress+Hauser Conducta GmbH+Co. KG, Gerlingen (DE)

(72) Inventors: Michael Weiss, Gerlingen (DE); Angela Eubisch, Nossen (DE); Michael Hanko, Dresden (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 151 days.

(21) Appl. No.: 15/279,101

(22) Filed: Sep. 28, 2016

(65) Prior Publication Data

US 2017/0089859 A1   Mar. 30, 2017

(30) Foreign Application Priority Data

Sep. 28, 2015   (DE) .................. 10 2015 116 357

(51) Int. Cl.
  *G01N 27/327*   (2006.01)
  *G01N 27/416*   (2006.01)
  (Continued)

(52) U.S. Cl.
  CPC ......... *G01N 27/4163* (2013.01); *G01N 21/05* (2013.01); *G01N 21/31* (2013.01);
  (Continued)

(58) Field of Classification Search
  CPC .. G01N 27/30–27/304; G01N 27/307–27/308; G01N 27/31–27/32; G01N 27/333; G01N 27/34; G01N 27/36; G01N 27/40; G01N 27/401; G01N 27/403; G01N 27/4035; G01N 27/404; G01N 27/4045; G01N 27/4163; G01N 27/4165; G01N 27/4166; G01N 27/4167; G01N 27/4168
  USPC ........ 204/404, 409, 412, 415–420, 431–433, 204/435; 205/787.5, 789–789.5, 205/792.5–793
  See application file for complete search history.

(56) References Cited

U.S. PATENT DOCUMENTS 3,997,420 A * 12/1976 Buzza ................ G01N 33/4925
                                                       204/411
4,342,964 A *  8/1982 Diamond ........... G01N 27/4165
                                                       324/438
(Continued)

FOREIGN PATENT DOCUMENTS

CH        469261 A    2/1969
CN       1041653 A    4/1990
(Continued)

OTHER PUBLICATIONS

Search Report for German Patent Application No. 10 2015 116 357.8, German Patent Office, dated Sep. 9, 2016, 11 pp.

*Primary Examiner* — Bach T Dinh
(74) *Attorney, Agent, or Firm* — Kelly J. Smith; PatServe (57) ABSTRACT

A sensor arrangement for determining at least one measurand of a measuring medium includes at least one first sensor with a first sensing element used to record measured values of a first measurand of the measuring medium, a housing having a housing wall which surrounds a housing interior containing the first sensing element, wherein the housing interior contains a medium in particular, a liquid which has a predetermined value of the first measurand.

6 Claims, 2 Drawing Sheets

(51) Int. Cl.
  *G01N 21/05* (2006.01)
  *G01N 21/31* (2006.01)
  *G01N 21/85* (2006.01)
  *G01N 27/30* (2006.01)
  *G01N 27/31* (2006.01)
  G01N 27/28 (2006.01)
  G01N 21/27 (2006.01)
  G01N 21/33 (2006.01)
  G01N 21/53 (2006.01)

(52) U.S. Cl.
  CPC ............ *G01N 21/85* (2013.01); *G01N 27/302* (2013.01); *G01N 27/31* (2013.01); *G01N 27/3272* (2013.01); *G01N 27/3274* (2013.01); G01N 21/274 (2013.01); G01N 21/33 (2013.01); G01N 21/534 (2013.01); G01N 27/283 (2013.01)

(56) References Cited

U.S. PATENT DOCUMENTS

| | | | |
|---|---|---|---|
| 5,511,408 | A | 4/1996 | Yoshioka et al. |
| 2011/0147213 | A1* | 6/2011 | Auerswald ............ G01N 27/36 204/415 |

FOREIGN PATENT DOCUMENTS

| | | |
|---|---|---|
| CN | 102405450 A | 4/2012 |
| DE | 3242457 A | 5/1984 |
| DE | 102010030874 A1 | 1/2012 |
| DE | 102013109105 A1 | 2/2015 |
| DE | 102014103328 A1 | 9/2015 |
| JP | 2011237354 A | 11/2011 |

* cited by examiner

SENSOR ARRANGEMENT

CROSS-REFERENCE TO RELATED APPLICATIONS

The present application is related to and claims the priority benefit of German Patent Application No. 10 2015 116 357.8, filed on Sep. 28, 2015, the entire contents of which are incorporated herein by reference.

TECHNICAL FIELD

The present disclosure relates to process sensors, particularly to in-line process sensors for disposable reactors.

BACKGROUND

Sensors are used to monitor biological, biochemical, or pharmaceutical processes. They are used to monitor a wide variety of measurands, such as flow rate, temperature, pressure, or analytical measurands. Analytical measurands are, for example, concentrations or activities of substances contained in the measuring medium to be monitored or variables correlated to them. Sensors are often stored in a process plant for long periods of time before they are commissioned. In pharmaceutical, biological, biochemical, or biotechnological processes, sensors are often sterilized before being used in a process.

Pharmaceutical, biological, biochemical, or biotechnological processes are increasingly being carried out by means of so-called disposable process solutions, e.g., in process plants in single-use technology. Such process plants comprise pipelines or reactors which are provided as disposable containers (otherwise known as disposables or disposable bioreactors, or single use bioreactors or single-use components). Such disposable containers can, for example, be flexible containers, e.g., bags, hoses, or fermenters. Bioreactors or fermenters often have supply and return lines which can, for example, be provided as hoses. Solid pipe sections can also be used in the supply and return lines. All of these disposable containers can be disposed of at the end of a process. In this way, complex cleaning and sterilization processes are avoided. In particular, the use of disposable containers prevents the risk of cross contamination, thereby increasing process reliability.

The processes performed in the disposable containers run in a closed system, i.e., without being connected to the environment outside the disposable containers. Since sterile conditions are often required, the disposable containers must be sterilized before the introduction of the process media. Gamma radiation is often used for this purpose in biochemical, biological, biotechnological, and pharmaceutical applications. Also, while the processes are running in a disposable fermenter or disposable reactor, foreign substances in particular, germs from the environment must be prevented from penetrating the inside of the process vessel, so that the process flow is not impaired or distorted. The same also applies to supply and return lines which terminate in the disposable fermenter or disposable reactor, or lead out of the disposable fermenter or disposable reactor.

In order to monitor or control processes in such disposable process plants it can, as is the case in conventional process plants, be necessary to measure physical or chemical measurands of the media contained in the process vessels. The measurands to be monitored can, for example, be temperature or analytical measurands, such as pH value, cell density, conductivity, optical transmission or absorption, or a concentration or activity of a chemical substance, e.g., of a specific type of ion of a specific element or of a specific compound, such as the content of dissolved oxygen or $CO_2$. In biotechnological processes, important measurands can also be so-called nutrient parameters, such as the glucose, glutamate, or lactose content of the process medium, or metabolic parameters of the microorganisms used in the processes.

At least some of the aforementioned measurands can be measured by means of optical sensors, for example: an absorption, transmission, or scattered light intensity and thus a cell density a turbidity; a concentration of specific chemical compounds present in the process medium; or a spectrometric or photometric sum parameter can be determined by irradiating the measuring medium with measuring radiation and by recording the measuring radiation intensity after interaction with the medium.

As an alternative to or in addition to optical sensors, electrochemical in particular, potentiometric sensors can be used, for example, to determine the pH value or an ion concentration in the process medium. Amperometric sensors for determining the dissolved oxygen content or the $CO_2$ content, and conductivity sensors that work on a conductive or inductive principle, can also be used.

These sensors can be integrated in the wall of a process vessel in which the process medium to be monitored is contained and/or can have a sensing element integrated in the wall of such a process vessel. Often, so-called in-line measuring systems are used to monitor measuring media flowing through pipelines. As a rule, in-line measuring systems have two connections which can, for example, be arranged opposite one another so that the in-line measuring system can be used in a line of a process plant by having the two connections linked to complementary connections in the line.

An in-line measuring system for measuring and monitoring several measurands, which can, for example, be used to monitor measurement parameters of a medium present, or possibly flowing, in a sterile liquid line of a biochemical, biotechnological, or pharmaceutical process, is known, for example, from U.S. Pat. No. 7,973,923. The sterile liquid line can be a process line of a conventional process plant or a process plant in single-use technology.

The in-line measuring system known from U.S. Pat. No. 7,973,923 comprises a flow-through cell with a supply line and a return line which each has a connection for linking to a line with process medium flowing through it, for example, of a process plant. Furthermore, two sensing elements for recording the values of two mutually different measurands, such as pH value, dissolved oxygen content, $CO_2$ content, concentrations of specific ions, conductivity, or temperature, are integrated by means of connections in the wall of the flow-through cell. The sensing elements integrated in the flow-through cell are in contact with the process medium flowing through the flow-through cell directly for recording measured values. Moreover, the flow-through cell has two mountings for a radiation source module and a radiation receiver module. The radiation source module and the radiation receiver module can be inserted opposite each other into the wall of the flow-through cell by fixing them in the mountings. Both modules each have a transparent window for the measuring radiation emitted by the radiation source, so that the radiation emitted by the radiation source encounters the radiation receiver after passing through the flow-through cell and after interaction with the process medium flowing through the flow-through cell. The radiation receiver is equipped to generate and output an electrical signal which is dependent upon the received radiation intensity. The signal is a measure of a third measurand which can be differentiated from the measurands that are recorded by means of the two sensing elements integrated in the flow-through cell. Therefore, by means of the sensing elements integrated in the wall of the flow-through cell and the optical sensor, measured values of three different measurands of process medium flowing through the flow-through cell can be recorded.

Before sensors are commissioned in a biotechnological, biochemical, or biological process plant, in particular of the type described above, the sensor must often be sterilized first, just like all the other components of the process plant. For this purpose, sensors or in-line measuring systems can be integrated in a process vessel of the plant and sterilized together with the vessel.

When the sensors undergo a storage period, as a result of the sterilization, and/or if there is a long period of time between sterilization and commissioning, properties of the sensing elements can change, which can lead to a change in the respective sensory characteristic curve, e.g., to a drift of the zero point. The sensing elements of potentiometric and amperometric sensors frequently comprise membranes that should ideally be stored in a damp atmosphere to ensure that the sensor provides reliable measured values immediately from the point of commissioning.

In addition to this, sterilization by means of gamma radiation, which is required for many biochemical and biotechnological processes, would lead to the destruction of electronic components in the sensors. For this reason, it is recommended, e.g., in DE 10 2011 080 956 A1, that sensors, or sensing elements integrated in flow-through cells, be arranged as analog sensing elements in the wall of disposable containers to be sterilized, and that they only be detachably connected to an electronic unit comprising non-sterilizable components after sterilization, said electronic unit being designed to process the analog measured values provided by the sensing element. The electronic unit can continue to be used after the end of the process and can be connected to a new sterilized disposable sensing element in a different process arrangement. Since the complete measuring chain of the sensor, which comprises the sensing element and the electronic unit, is not available until commissioning, a calibration or adjustment directly prior to commissioning would also be desirable in such cases.

Therefore, in many applications there is a need for an option for storing sensors or sensing elements in a damp atmosphere and for an efficient calibration and/or verification of sensors shortly before or upon commissioning.

BRIEF SUMMARY

It is, therefore, the aim of the present disclosure to specify a sensor arrangement and a process that enables one or several sensors to be operated with sufficient measurement accuracy and measurement quality.

The sensor arrangement according to the present disclosure for determining at least one measurand of a measuring medium includes at least one first sensor with a first sensing element used to record measured values of a first measurand of the measuring medium, and a housing having a housing wall which surrounds a housing interior containing the first sensing element, wherein the housing interior contains a medium in particular, a liquid which has a predetermined value of the first measurand.

Due to the fact that the sensing element is arranged in a self-contained housing interior, storage in the medium over a long period of time is possible for example, storage in a damp atmosphere, if the medium is a liquid. Since the medium has a defined value of the measurand, it can also serve as a calibration medium in addition to its function as a storage medium. In this way, by recording a measured value of the first measurand in the medium contained in the housing interior using the first sensing element, it is possible to calibrate or adjust the first sensor upon commissioning or shortly before commissioning. It is, in particular, possible to perform a one-point calibration with the help of the value of the first measurand recorded by the first sensor. In the case of sensors that are only slightly chemically, mechanically, or thermally loaded, this type of calibration and/or adjustment based upon a single measuring point is often sufficient to identify a change in the sensor in particular, a change in the sensor characteristic curve caused by the storage and/or sterilization of the sensor prior to commissioning and, where applicable, to compensate for it by making adjustments.

The housing and the integrated first sensing element can be sterilized with the medium contained therein, e.g., by means of irradiation using gamma radiation and/or beta radiation. The radiation dose thereby used is at least 25 kGy, and preferably at least 40 kGy, or even above 50 kGy. The medium is preferably selected such that the predetermined value of the first measurand does not change during this irradiation.

In general, calibration is understood to mean checking the display of a measuring device against a standard. The deviation between true value and display value is determined. This step is referred to as verification. The alignment of the display value with the true value is referred to as adjusting. Here and below, the terms "adjustment," "verification," and "calibration" are used within the meaning of these definitions.

The sensor comprises a data processing unit, in whose memory a characteristic curve is stored and which determines the measured values of the first measurand by means of the characteristic curve from the measuring signals of the first sensing element. For example, the sensing element can be provided separately from the data processing unit and/or detachably connected to the data processing unit. In this case, the sensing element has electrical connections which are connected to the data processing unit via a cable connection for transferring measured values, wherein the sensing element and the data processing unit together form the sensor. The sensing element records the physical measurand and outputs an analog or digital signal which is dependent upon the measurand, as a raw measured value. In this case, the data processing unit is designed to convert raw measured values obtained via the cable connection to a measured value of the first measurand in the physical unit of the measurand by means of the characteristics curve, and to output them.

In one embodiment, the first sensing element has a membrane which is in contact with the medium. Storage in a damp atmosphere is advantageous for many sensing elements with membranes, such as potentiometric or amperometric sensing elements, so that the medium in this embodiment is preferably a liquid.

In a further embodiment, the first sensing element can be a potentiometric sensing element which comprises a reference half-cell, wherein the reference half-cell comprises a reference electrolyte which is in contact with the medium via a crossover, such as a diaphragm, and wherein the medium is a liquid which has the same composition as the reference electrolyte. By preventing concentration gradients in this way via the crossover, it can be ensured that the compositions of the reference electrolyte, and of the liquid that serves as storage and/or calibration medium for the first sensor, do not change, even during long periods of storage.

The first sensing element can, for example, be a potentiometric pH sensing element with a measuring half-cell comprising a pH glass membrane and the aforementioned reference half-cell. In this embodiment, the medium contained in the housing interior is advantageously a pH buffer solution in particular, a phosphate buffer solution with a halide concentration, especially, a chloride concentration which is consistent with that of the reference electrolyte of the reference half-cell.

In one embodiment, the sensor arrangement can have at least one connection device by means of which the sensor arrangement can be integrated in a process vessel in particular, by which it can be connected with one or a plurality of process vessel connections complementary to the connection device. The sensor arrangement, including its housing, can, therefore, be linked to the process vessel. This allows for simultaneous sterilization of the sensor arrangement with the process vessel, such as by means of the aforementioned radiation doses. Upon commissioning of the sensor arrangement, the housing that surrounds the housing interior that contains the first sensing element and closes up towards the process vessel can be removed or be opened up towards the process vessel in such a way that the process medium contained in the process vessel can be brought into contact with the first sensing element to record measured values.

Further, the sensor arrangement comprises at least one second sensor with a second sensing element arranged inside the housing interior, which is designed to record values of a second measurand which is, in particular, different from the first measurand of the measuring medium, and wherein the medium contained in the housing interior has a predetermined value of the second measurand.

The second sensor can have a data processing unit analogous to the first sensor alongside the second sensing element, in whose memory a characteristic curve is stored, and which determines measured values of the second measurand with the aid of the characteristic curve from the measuring signals of the second sensing element. The sensing element of the second sensor can be separate from the data processing unit and/or detachably linked to the data processing unit. In this case, the second sensing element has electrical connections for transferring measured values which are linked to the data processing unit via a cable connection, wherein the second sensing element and the data processing unit together form the second sensor. The second sensing element records the second measurand and outputs an electrical signal, which is dependent upon the second measurand, as a raw measured value. In this case, the data processing unit is designed to convert raw measured values obtained via the cable connection by means of the characteristic curve to a measured value of the second measurand in the physical unit of the measurand. The data processing units of the first and second sensors can be realized in a single device, such as a multi-channel transformer.

In an embodiment, the sensor arrangement is designed as a prefabricated in-line measuring system, wherein the housing is designed as a flow-through cell having a cuvette, a supply line terminating in the cuvette, and a return line terminating in the cuvette, wherein, at the end facing away from the cuvette, the supply line and the return line each has a connection which closes the flow-through cell of the prefabricated in-line measuring system liquid-tight and which can be linked to a process vessel in particular, a medium service line and wherein the first sensing element is integrated in the flow-through cell in particular, in the cuvette.

The prefabricated in-line measuring system for determining at least one measurand of a measuring medium therefore includes: a flow-through cell having a cuvette, a supply line terminating in the cuvette, and a return line terminating in the cuvette, wherein, at the end facing away from the cuvette, the supply line and the return line each has a connection which closes the flow-through cell of the prefabricated in-line measuring system liquid-tight and which can be linked to a process vessel in particular, a medium service line; a first sensor with a first sensing element used to record values of a first measurand of the measuring medium, wherein the first sensing element is integrated in the flow-through cell in particular, in the cuvette; and a medium contained in the flow-through cell in particular, the cuvette filling the supply line and the return line, which has a predetermined value of the first measurand.

The supply line terminating in the cuvette and the return line terminating in the cuvette can be designed as hoses. They can have connections serving as sterile connectors on the ends facing away from the cuvette. Such sterile connectors are designed to be linked to complementary sterile connectors of the process line in which the in-line measuring system is to be used, such as hose lines in biological or biotechnological process plants, so as to create a mechanical connection between the hose line and the supply line or the return line of the flow-through cell. The sterile connectors and their complementary counterparts arranged in the lines of the process plant also have means of closure which ensure sterile closure of the supply and return lines or the process line. By activating the means of closure, after the connectors have been mechanically connected to their corresponding complementary counterparts of the process line, a fluid communication can be established between the process line and the return line, or the process line and the supply line. These types of sterile connectors are commercially available.

Further, the in-line measuring system can comprise at least one second sensor with a second sensing element, which is designed to record values of a second measurand of the measuring medium, wherein the medium contained in the flow-through cell also has a predetermined value of the second measurand.

In such an embodiment, the second sensor can have a data processing unit analogous to the first sensor alongside the second sensing element, in whose memory a characteristic curve is stored, and which determines measured values of the second measurand with the aid of the characteristic curve from the measuring signals of the second sensing element. The sensing element of the second sensor can be separate from the data processing unit and/or detachably linked to the data processing unit. In this case, the second sensing element has electrical connections for transferring measured values which are linked to the data processing unit via a cable connection, wherein the second sensing element and the data processing unit together form the second sensor. The second sensing element records the second measurand and outputs an electrical signal, which is dependent upon the second measurand, as a raw measured value. In this case, the data processing unit is designed to convert raw measured values obtained via the cable connection by means of the characteristic curve to a measured value of the second measurand in the physical unit of the measurand. The data processing units of the first and second sensors can be realized in a single device, such as a multi-channel transformer.

The first and the second sensing element can be arranged in the wall of the flow-through cell in particular, of the cuvette in such a way that, for example, by means of an adapter, at least one immersed section of the first sensing element and an immersed section of the second sensing element intended to be in contact with the measuring medium are located inside the flow-through cell in particular, the cuvette.

The medium contained in the flow-through cell can be a liquid which essentially fills the supply line, return line, and the cuvette, so that the first and second sensing elements are in contact with the liquid for recording a value of the first and the second measurands.

In a further embodiment of the in-line measuring system, the first sensor is a pH sensor, and the second sensor is a conductivity sensor. The pH sensor can, for example, be a potentiometric sensor, and the second sensor can be an inductive or conductive conductivity sensor. Other variables which can be considered as first or second measurands are, for example, $CO_2$ content, ion concentrations, dissolved oxygen content, and glucose content.

In such an embodiment, the medium can be an aqueous solution which has a predetermined conductivity resulting from its composition of between 10 μS/cm and 300 mS/cm alternately, between 10 μS/cm and 50 mS/cm and which also, as a result of the composition of the liquid, has a predetermined pH value of between 3 and 9, alternately, between 6 and 8.

The aqueous solution can, for example, comprise a buffer system in particular, a phosphate buffer with a phosphate concentration of 0.01 to 0.5 mol/L, such as between 0.01 and 0.05 mol/L. In addition, the solution can contain sodium chloride and/or potassium chloride. If the solution contains only sodium chloride, its concentration can be between 0.01 and 3.5 mol/L e.g., between 0.1 and 0.2 mol/L. If the solution contains only potassium chloride, its concentration can likewise be between 0.01 and 3.5 mol/L e.g., between 0.1 and 0.2 mol/L. If the solution contains both sodium chloride and potassium chloride, its overall concentration can be between 0.01 and 3.5 mol/L e.g., between 0.1 and 0.2 mol/L. For example, the solution can be a phosphate-buffered saline solution with 0.01 mol/L phosphate in the buffer system $H_2PO_4^-/HPO_4^{2-}$ and an NaCl concentration of 0.01 to 3.5 mol/L or between 0.01 and 0.05 mol/L.

The cuvette can have a wall which includes a first wall section which is transparent to measuring radiation of a predetermined wavelength or of a predetermined wavelength range in particular, to measuring radiation of the UV spectral range, of the visible spectral range, or of the IR spectral range and which includes a second wall section facing the first wall section and essentially running parallel to it, which is transparent to the measuring radiation. For example, the cuvette can have a window, or the cuvette in its entirety can consist of a material that is transparent to the measuring radiation. This embodiment of the cuvette allows the measuring radiation to radiate through the transparent wall sections and through the medium contained in the cuvette. The intensity of the measuring radiation after passing through the cuvette or after diffusing in the cuvette allows the spectrometrically or photometrically recordable measurands, e.g., concentrations of specific substances, cell densities, or turbidity, to be determined. A radiation source and a radiation receiver can be mechanically coupled to the wall of the flow-through cell from outside.

The prefabricated in-line measuring system can, for example, in an advantageous embodiment, further have an optical sensor for recording a third measurand, which is, in particular, different from the first or second measurand, and which includes a radiation source and a radiation receiver, wherein the radiation source is arranged in such a way in relation to the cuvette that measuring radiation emitted by the radiation source enters the cuvette through a first section of a wall of the cuvette which is transparent to the measuring radiation, and wherein the radiation receiver is arranged in such a way in relation to the radiation source and in relation to the cuvette that the measuring radiation encounters the radiation receiver through the first or a second section of the wall of the cuvette which is transparent to the measuring radiation. The third measurand can, alternatively, also be the same measurand as the first or the second measurand.

One or a plurality of light-emitting diodes or one or a plurality of laser diodes can be considered as a radiation source. One or a plurality of photodiodes, a photodiode array, or a CCD array or a CCD line can serve as a radiation receiver.

The radiation source and the radiation receiver can, for example, as described in U.S. Pat. No. 7,973,923, be arranged respectively in a radiation source module and a radiation receiver module. These modules can each comprise a housing which can be attached to the flow-through cell, inside which are arranged the radiation source or the radiation receiver, and electrical or electronic circuits for operating the radiation source or for generating and outputting an electrical signal which is used as a raw measured value and which is dependent upon the intensity of the radiation encountering the receiver. Further, the optical sensor can comprise a data processing unit which determines and outputs a value of the third measurand with the aid of the raw measured value received by the receiver.

In such an embodiment, the radiation source and the radiation receiver can also be accommodated in an individual housing which includes a recess in which the flow-through cell in particular, the cuvette of the flow-through cell can be arranged. In this embodiment, the housing has a first window through which the measuring radiation of the radiation source can exit the housing and a second window in particular, facing the first window through which measuring radiation can re-enter the housing after passing through an optical path leading through the recess. The sections of the wall of the cuvette which are transparent to the measuring radiation can be aligned flush with the windows, so that the measuring radiation also penetrates the cuvette along the optical path running between the windows.

In this embodiment, the medium contained in the flow-through cell can also have a value of the third measurand which is predetermined by its composition. The third measurand can be an absorption or transmission, or a turbidity or a cell density.

Advantageously, the medium in the wavelength range of the measuring radiation has an absorption between 0 $cm^{-1}$ and 0.1 $cm^{-1}$ preferably, of less than 0.02 $cm^{-1}$. This is the case, for example, with the aforementioned aqueous phosphate-buffered NaCl and/or KCl solution.

The medium can be a liquid which essentially fills the supply line, return line, and the cuvette, so that an optical measurement path running between the radiation source and the radiation receiver runs through the liquid.

The present disclosure also includes a method for commissioning a sensor arrangement in particular, a sensor arrangement in accordance with one of the previously described embodiments which has a housing wall surrounding a housing interior, wherein the method includes: the recording of a value of a first measurand of a medium contained in the closed housing interior, which has a predetermined value of the first measurand, by means of a first sensing element of a first sensor, wherein the first sensing element is arranged in the housing interior; and the performance of a calibration and/or verification and/or adjustment of the first sensor with the aid of the recorded value of the first measurand.

The method can further comprise the linking of the sensor arrangement with a process vessel. This process step can be carried out after the recording of the first measurand by means of the first sensing element of the first sensor and the performance of the calibration. This is conceivable, for example, if the sensing element is stored for a longer period in the medium and is calibrated and/or verified and/or adjusted in the same medium shortly before commissioning and is then integrated and commissioned in a process plant for carrying out process monitoring.

Alternatively or additionally, the sensor arrangement, including the housing, is mechanically linked with the process vessel before the recording of a value of the first measurand of the medium contained in the closed housing interior and before the calibration, verification, and/or adjustment of the first sensor is carried out. This is advantageous, for example, in applications in disposable process solutions in which the sensor arrangement, with the housing and the medium contained therein serving both as storage and as calibration medium, is integrated in a disposable process vessel and sterilized together with the same, and then commissioned after a longer storage period. In this way, the calibration and/or verification and/or adjustment can be carried out after the storage period shortly before or upon commissioning of the disposable process vessel and the sensor arrangement integrated therein.

The method can further comprise: the recording of a value of a second measurand of the medium contained in the housing which is closed with respect to the process vessel, with the medium having a predetermined value of the second measurand, by means of a second sensing element of a second sensor, wherein the second sensing element is arranged in the housing interior, and the performance of a calibration and/or verification, and/or adjustment of the second sensor with the aid of the recorded value of the second measurand.

In a further process step which, depending upon the application, can take place before the sensor arrangement is linked to the process vessel or not until after calibration and/or adjustment of the first sensor, and, possibly, of a second and/or additional sensors of the sensor arrangement, a fluid communication is established between the housing interior and the process vessel.

Advantageously, the sensor arrangement is designed as a prefabricated in-line measuring system in accordance with one of the embodiments described above.

The present disclosure also includes a method for commissioning such an in-line measuring system having a flow-through cell, a cuvette, a supply line terminating in the cuvette, and a return line terminating in the cuvette, wherein, at the end facing away from the cuvette, the supply line and the return line each has a connection, e.g., a sterile connector, which closes the flow-through cell of the prefabricated in-line measuring system liquid-tight and which can be linked to a process vessel in particular, a medium service line wherein the method includes: mechanical linking of the connection closing the supply line with a first connection complementary to this connection of the process vessel and of the connection closing the return line with a second connection complementary to this connection of the process vessel; the recording of a value of a first measurand of a medium contained in the flow-through cell, which is still closed with respect to the process vessel, said medium having a predetermined value of the first measurand, by means of a first sensing element of a first sensor which is integrated in the flow-through cell in particular, in the cuvette, and the performance of a calibration and/or verification and/or an adjustment of the first sensor with the aid of the recorded value of the first measurand.

The performance of the calibration can include the step of the recording of a measured value of the first measurand of the medium as current calibration measured value by means of the first sensing element, and the comparison of the calibration measured value with the previously known value of the first measurand of the medium.

The performance of the adjustment can include the steps: the recording of a measured value of the first measurand of the medium as current calibration measured value by means of the first sensing element; the comparison of the calibration measured value with the previously known value of the first measurand of the medium; and the updating of a calculation method or characteristic curve in a memory allocated to the first sensing element, which is used to determine a measured value from a measuring signal of the first sensing element, with the aid of the comparison.

The method can further include: the recording of a value of a second measurand of the medium contained in the flow-through cell, which is still closed with respect to the process vessel, said medium having a predetermined value of the second measurand, by means of a second sensing element which is integrated in the flow-through cell in particular, in the cuvette, and the performance of a calibration and/or verification and/or adjustment of the second sensor with the aid of the recorded value of the second measurand.

A calibration and or an adjustment of the second sensor can be performed in the same way as previously described for the first sensor.

The method can further include: the recording of a value of a third measurand by means of an optical sensor which includes a radiation source and a radiation receiver, wherein the radiation source emits measuring radiation which enters a cuvette through a first section of a wall of the cuvette which is transparent to the measuring radiation, and passes through the medium and exits the cuvette again through a second section of the wall of the cuvette which is transparent to the measuring radiation, and encounters the radiation receiver, which generates an electrical signal which is dependent upon the intensity of the measuring radiation encountering the radiation receiver, and the performance of a calibration and/or verification and/or an adjustment of the optical sensor with the aid of the recorded value of the third measurand.

A calibration and or an adjustment of the optical sensor can be performed analogously to that previously described for the first sensor.

The method can further include the establishment of a fluid communication between the supply line, the return line, and the process vessel.

The medium contained in the housing or, if the housing is designed as a flow-through cell, the medium contained in the flow-through cell, can run off into the process vessel, e.g., through the return line of the flow-through cell, after the fluid communication has been established. To monitor a medium flowing through the process vessel, said medium can be fed through the flow-through cell. If the sensor arrangement or the in-line measuring system is used in a biotechnological or biochemical process that is to be kept sterile, it is therefore advantageous for the sections of the flow-through cell communicating with the process vessel by the connection using sterile connectors and the medium contained in the flow-through cell to be sterile or to be sterilized in advance for example, by means of irradiating with gamma radiation.

The present disclosure is described in detail below with reference to the exemplary embodiments illustrated in the figures.

BRIEF DESCRIPTION OF THE DRAWINGS

The present disclosure is explained in further detail below on the basis of the exemplary embodiments shown in the figures.

DETAILED DESCRIPTION

Figure 1:
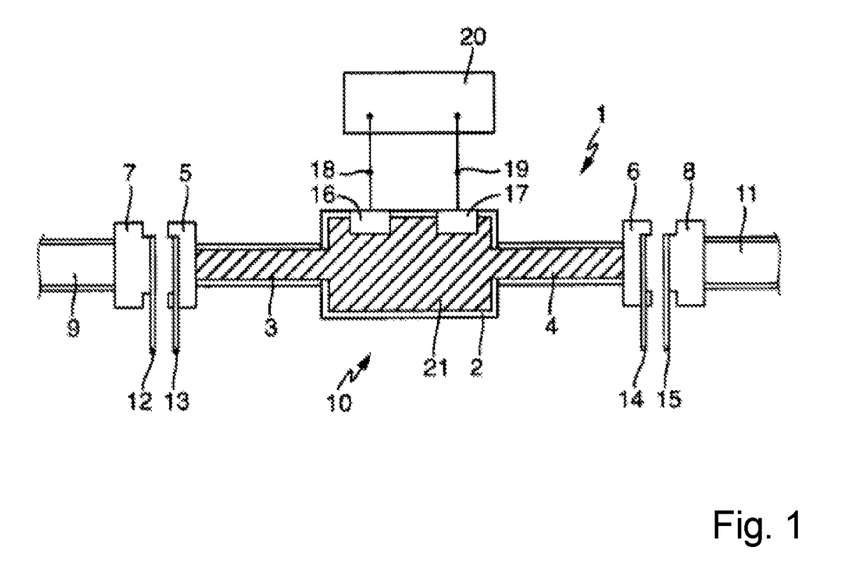
FIG. 1 shows a schematic longitudinal diagram of a flow-through cell with two integrated electrochemical sensors, according to an exemplary embodiment of the present disclosure.

FIG. 1 shows a schematic diagram of an in-line measuring system 1 with a flow-through cell 10 having a cuvette 2, a supply line 3 terminating in the cuvette 2, and a return line 4 terminating in the cuvette 2. The cuvette 2 can, for example, consist of a plastic; similarly, the supply line 3 and the return line 4 can consist of a plastic. The supply line 3 and the return line 4, as in the example shown here, can be flexible hose lines. The supply line 3 and the return line 4 are closed so as to be sterile by means of a sterile connector 5, 6 on their respective ends facing away from the cuvette 2. The sterile connectors 5, 6 have locking means by means of which they can be mechanically linked with complementary sterile connectors 7, 8 of a liquid line of a process plant, e.g., of a peripheral line of a fermenter or reactor. In this way, the in-line measuring device 1 can, for example, be linked with its supply line 3 to a first section 9 of a process line, and, with its return line 4, to a second section 11 of a process line and thus be used in the process line. Even after the mechanical linking of the sterile connectors 5, 7, 6, and 8, the flow-through cell is still closed liquid-tight and so as to be sterile with respect to the process line by means of the membranes 12, 13, 14, and 15. To establish a fluid communication between the flow-through cell 2 and the process line, the membranes 12, 13, 14, 15 are pulled out of the linked connectors.

Two sensing elements 16, 17 are integrated in the wall of the cuvette 2. In the present example, the first sensing element 16 is a pH sensing element, and the second sensing element 17 is a conductivity sensing element. Both sensors have connections 18, 19 via which they are detachably connected to a separate electronic unit 20, which can, for example, be a multi-channel transducer. The electronics unit 20 can have means for digitizing an electrical measuring signal provided by the sensors 16, 17, as well as a data processing unit, which is designed to process the digital signals. The processing includes, in particular, the determination of measured values of the measurands, pH value, and conductivity from the raw measured values provided by the sensing elements. In the present example, both sensing elements 16, 17 are linked to a single electronics unit 20. In an alternative embodiment it is, of course, possible for a dedicated electronics unit to be assigned to each sensing element. Similarly, it is possible for the sensing elements to be designed to already output digital measuring signals to the electronics unit.

A medium 21 filling the cuvette 2, the supply line 3, and the return line 4 is contained in the flow-through cell 10, said medium having a known pH value predetermined by its composition and a correspondingly known conductivity. The first sensing element 16 has a sensor element, such as a pH-sensitive membrane, which has to be brought into contact with a measuring medium to record pH measured values. The sensing element 16 is designed to generate and output an electrical signal which is dependent upon the pH value of the measuring medium in contact with the sensor element. For example, the sensing element 16 can be a potentiometric sensing element which outputs a voltage dependent upon the pH value. The medium 21 contained in the cuvette 2 in the present case fills the cuvette 2 to the extent that the sensor element of the sensing element 16 is in contact with the medium 21 and can therefore record a pH measured value of the medium 21.

The second sensing element 17 also has a section specifically for contact with a measuring medium for recording conductivity measured values. In the present example, the immersion area of the sensing element 17 includes electrodes for a conductive conductivity measurement. In the present case, the cuvette 2 is filled by the medium 21 to such an extent that the immersion area of the second sensing element is in contact with the medium 21 to record a conductivity measured value.

In the present example, it is possible to sterilize the flow-through cell 10 with the medium 21 contained therein and the sensing elements 16, 17 before their use in the process line, e.g., by means of irradiation with gamma radiation. In this way, all sections of the flow-through cell 10 and the sensing elements 16, 17, which can subsequently come into contact with a process medium flowing through the process line in which the in-line measuring device is used, can be sterilized.

Figure 2A:
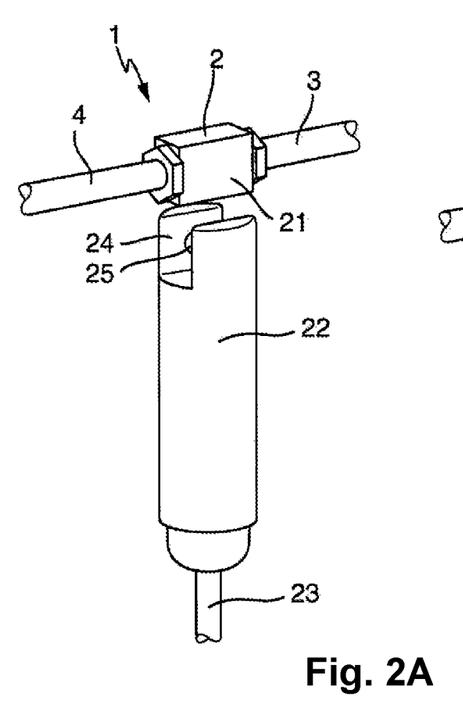
FIGS. 2A, 2B and 2C show exemplary embodiments the flow-through cell according to FIG. 1 with an additional optical sensor according to the present disclosure.
Figure 2B:
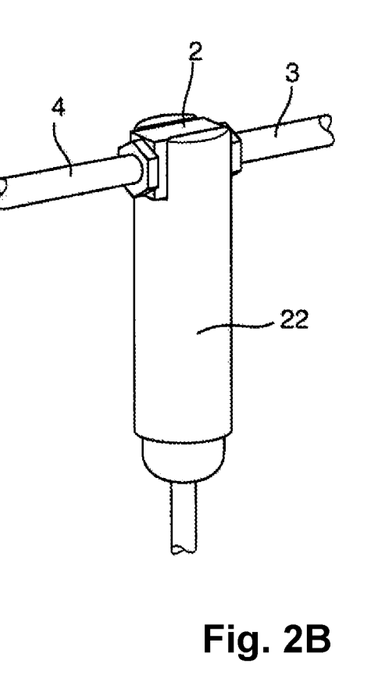
Figure 2C:
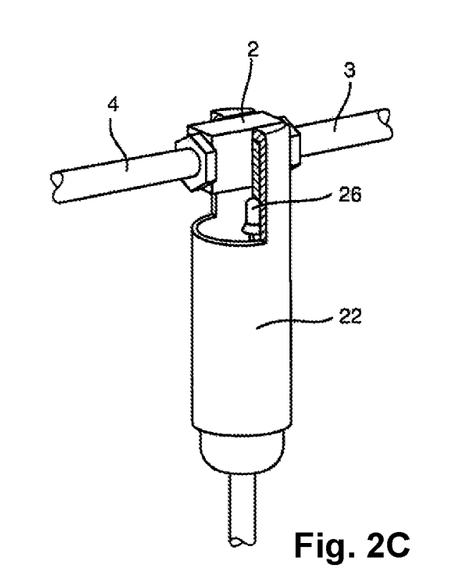

FIGS. 2A-C shows a schematic representation depicting the in-line measuring system 1 described with the aid of FIG. 1, with an additional optical sensor 22. For purposes of clarity, the first and the second sensing elements 16, 17 are not shown in FIGS. 2A-C.

The optical sensor 22 is designed to record absorption or transmission measured values of measuring radiation irradiated through the cuvette 2. The sensor 22 has a housing that has a recess on a front side 24, in which the cuvette 2 can be inserted. FIG. 2A shows the optical sensor 22 separated from the flow-through cell 10, while FIG. 2B shows the sensor 22 with the cuvette 2 inserted in the recess 24. The housing of the optical sensor 22 has windows 25 on two opposing walls, said windows being flush with the transparent wall sections of the cuvette 2 when the cuvette 2 is inserted.

A radiation source 26 in the present example, a UV light-emitting diode is arranged inside the housing of the sensor 22 (FIG. 2C). Inside the housing of the sensor 22, there is also a radiation receiver which is designed as a photo diode (not visible in FIG. 2C). The radiation source 26 and the radiation receiver are arranged in the housing such that the radiation emitted by the radiation source 26 escapes as measuring radiation through one of the windows 24 arranged in the housing wall, passes through the cuvette 2, and encounters the radiation receiver after entering through the opposite window. Optical elements and/or light conductors can be provided for this purpose for beam formation and control. The wall sections of the cuvette 2 which are flush with the windows are transparent to the measuring radiation UV radiation in the present example so that the radiation intensity of the measuring radiation encountering the radiation receiver is essentially determined by the absorption of a measuring medium contained in the cuvette 2. Depending upon the impinging radiation intensity, the radiation receiver designed as a photo diode generates an electrical digital or analog signal, which can be output via the line 23 to an electronics unit. In the present example, the sensor 22 is linked to the electronics unit 20 (FIG. 1) via the line 23, which thus records and processes the measuring signals, both from the sensing elements 15 and 16 integrated in the flow-through cell 10 and from the optical sensor 22. In the present case, the electronics unit 20 is designed to determine an absorption measured value from the raw electrical signal generated by the radiation receiver with the aid of a calculation rule based upon the Beer-Lambert Law.

In the present example, the medium 21 filling the flow-through cell 10 has an absorption of below 0.02 for the measuring radiation of the optical sensor 22. It can, therefore, be used to calibrate or adjust or zero balance the optical sensor 22.

The electronics unit 20 is designed for the purpose of performing in the medium 21 a calibration and/or adjustment and/or verification of the sensing elements 16, 17 and of the optical sensor 22 prior to establishing a fluid communication between the flow-through cell 10 and the process line by removing the membranes 12, 13, 14, and 15.

For the calibration, the electronics unit 20 triggered, for example, by means of an input by operating personnel when commissioning the device records a pH measured value by means of the first sensing element 16, a conductivity measured value by means of the second sensing element 17, and an absorption measured value for the medium 21 by means of the optical sensor 22. To determine measured values from the measuring signals supplied by the sensing elements 16, 17 and the sensor 22, calibration functions or characteristic curves are saved in the electronics unit, e.g., in the form of a calculation rule or a table, with the aid of which the electronics unit 20 determines a corresponding value for the measurand with the correct physical units, e.g., a pH measured value, from a measuring signal, e.g., a voltage value.

The actual values of these measurands in the medium 21, which are dictated by the composition of said medium, are stored in a memory of the electronics unit 20. For verification purposes, the electronics unit 20 compares the measured values determined from the recorded measuring signals with the stored values.

The electronics unit 20 can also perform an adjustment. To this end, the electronics unit 20, with the aid of the comparison of the measured values determined by means of the sensing elements 16, 17 and the optical sensor 22 with the stored values for the corresponding measurands, determines an adjustment value with which the measured values determined in the future with the aid of the stored calculation rules, e.g., by multiplication or division, are adjusted respectively. Alternatively, the electronics unit can adjust the stored calculation rules, e.g., the calibration functions, accordingly.

The composition of the medium 21 is to be selected in accordance with the measurands to be recorded by the sensing elements or the optical sensor in such a way that it has stable, predetermined values for the measurands to be recorded, even after sterilization. In the present example, in which the measurands are pH value, conductivity, and absorption, a suitable multi-standard medium of this type is an aqueous buffer solution with defined conductivity and an absorption close to zero in particular, smaller than 0.02 for UV radiation, especially in a UV range that is typically used for the photometric determination of biological molecules that is, between 230 and 280 nm.

A phosphate buffer solution has proved to be suitable for a combination of the measurands pH value, conductivity, and absorption in the specified UV range. The solution may also contain sodium chloride or potassium chloride, if required. Phosphate buffer systems are frequently used in biological applications and can be produced using purely inorganic components which do not demonstrate absorption in the wavelength range of the measuring radiation that is, between 230 and 280 nm. NaCl and KCl solutions also demonstrate sufficiently low absorption in the UV range between 230 and 280 nm that is, an absorption below 0.02. Therefore, a phosphate-buffered saline solution with a phosphate concentration in the buffer system $H_2PO_4^-/HPO_4^{2-}$ of 0.01 mol/L is particularly suitable. In order to reliably ensure that the buffer capacity is sufficient, even when minimal interaction of the solution with the materials in the flow-through cell occurs, a higher phosphate concentration of 0.025 mol/L to 0.05 mol/L can also be selected. This phosphate buffer solution can additionally contain physiological concentrations of NaCl and/or KCl, wherein the overall concentration of KCl and NaCl can be between 0.1 to 0.2 mol/L. Such a solution has a pH value of 7.4 and a conductivity of 10 to 30 mS/cm.

The invention claimed is:

1. A method for commissioning a sensor arrangement comprising the steps:
   providing a sensor arrangement, the sensor arrangement comprising a first sensor with a first sensing element configured to record values of a first measurand, and a housing having a housing wall defining a housing interior, the housing interior containing the first sensing element and a calibration medium having a predetermined value of the first measurand;
   mechanically linking the sensor arrangement with a process vessel without establishing fluid communication between the sensor arrangement and the process vessel;
   recording a value of the first measurand of the calibration medium by means of the first sensing element before establishing fluid communication between the sensor arrangement and the process vessel;
   performing a calibration, and/or a verification, and/or an adjustment of the first sensor using the recorded value of the first measurand before establishing fluid communication between the sensor arrangement and the process vessel;
   removing a membrane to establish fluid communication between the sensor arrangement and the process vessel; and
   permitting mixing of the calibration medium and the measuring medium after the removing step.

2. The method according to claim 1, the method further comprising:
   providing a sensor arrangement which further comprises a second sensor with a second sensing element, the second sensing element disposed inside the housing interior, the second sensor configured to record values of a second measurand of the calibration medium different from the first measurand, wherein the calibration medium has a predetermined value of the second measurand;
   recording the value of the second measurand by means of the second sensing element; and performing a calibration, and/or a verification, and/or an adjustment of the second sensor using the recorded value of the second measurand.

3. A method for commissioning a sensor arrangement comprising the steps:
providing a sensor arrangement, the sensor arrangement comprising a first sensor with a first sensing element configured to record values of a first measurand, and a housing having a housing wall defining a housing interior, the housing interior containing the first sensing element and a calibration medium having a predetermined value of the first measurand;
mechanically linking the sensor arrangement with a process vessel without establishing fluid communication between the sensor arrangement and the process vessel;
recording a value of the first measurand of the calibration medium by means of the first sensing element before establishing fluid communication between the sensor arrangement and the process vessel;
performing a calibration, and/or a verification, and/or an adjustment of the first sensor using the recorded value of the first measurand before establishing fluid communication between the sensor arrangement and the process vessel; and
establishing fluid communication between the sensor arrangement and the process vessel;
providing a sensor arrangement which further comprises a second sensor with a second sensing element, the second sensing element disposed inside the housing interior, the second sensor configured to record values of a second measurand of the calibration medium different from the first measurand, wherein the calibration medium has a predetermined value of the second measurand;
recording the value of the second measurand by means of the second sensing element and
performing a calibration, and/or a verification, and/or an adjustment of the second sensor using the recorded value of the second measurand;
providing a sensor arrangement further comprising:
a flow-through cuvette, the first sensing element and the second sensing element disposed in the cuvette,
a supply line terminated in the cuvette, the distal end of the supply line including a liquid-tight closure, and
a return line terminating in the cuvette, the distal end of the return line including a liquid-tight closure, where each of the supply line and the return line are connectable to a process vessel, where the cuvette comprises a first wall section and a second wall section facing the first wall section and running substantially parallel to the first wall section, the first wall section and the second wall section transparent to measuring radiation of a predetermined wavelength range;
mechanically linking the closure of the supply line with a first complementary connection of a process vessel wherein the mechanical linking does not include fluid communication between the process vessel and the cuvette;
mechanically linking the closure of the return line with a second complementary connection of the process vessel wherein the mechanical linking does not include fluid communication between the process vessel and the cuvette;
wherein the step of recording the value of the first measurand by means of the first sensing element is performed after the step of mechanically linking the closure of the return line with a second complementary connection of the process vessel;
wherein the step of performing a calibration, and/or a verification, and/or an adjustment of the first sensor using the recorded value of the first measurand is performed after the step of mechanically linking the closure of the return line with the second complementary connection of the process vessel.

4. The method according to claim 3, wherein the step of recording a value of a second measurand by means of the second sensing element is performed after the step of mechanically linking the closure of the return line with the second complementary connection of the process vessel; and
wherein the step of performing a calibration, and/or a verification, and/or an adjustment of the second sensor using the recorded value of the second measurand is performed after the step of mechanically linking the closure of the return line with the second complementary connection of the process vessel.

5. The method according to claim 4 the method further comprising:
providing a sensor arrangement further comprising an optical sensor configured to record values of the calibration medium of a third measurand different from the first measurand and the second measurand, the optical sensor comprising a radiation source and a radiation receiver, wherein the radiation source and the radiation receiver are disposed such that measuring radiation emitted by the radiation source traverses the first wall section and subsequently the second wall section and is received by the radiation receiver;
recording a value of the third measurand by means of the optical sensor; and
performing a calibration, and/or a verification, and/or an adjustment of the optical sensor using the recorded value of the third measurand.

6. The method according to claim 3, the method further comprising establishing a fluid communication between the supply line, the return line, and the process vessel.

* * * * *